US006171808B1

(12) United States Patent
Squirrell et al.

(10) Patent No.: US 6,171,808 B1
(45) Date of Patent: *Jan. 9, 2001

(54) MUTANT LUCIFERASES

(75) Inventors: David J Squirrell, Salisbury;
Christopher R Lowe, Cambridge;
Peter J White, Cambridge; James A H Murray, Cambridge, all of (GB)

(73) Assignee: The Secretary of State for Defence in Her Britannic Majesty's Government of the United Kingdom of Great Britain and Northern Ireland, Hampshire (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/875,277

(22) PCT Filed: Jan. 19, 1996

(86) PCT No.: PCT/GB96/00099

§ 371 Date: Oct. 1, 1997

§ 102(e) Date: Oct. 1, 1997

(87) PCT Pub. No.: WO96/22376

PCT Pub. Date: Jul. 25, 1996

(30) Foreign Application Priority Data

Jan. 20, 1995 (GB) .................................................. 9501172
Apr. 24, 1995 (GB) .................................................. 9508301

(51) Int. Cl.[7] ............................. C12N 9/02; C12N 15/53; C12N 1/21; C12Q 1/66
(52) U.S. Cl. ........................... 435/8; 435/189; 435/320.1; 435/252.3; 435/252.33; 435/254.21; 536/23.2
(58) Field of Search .................................. 435/189, 320.1, 435/252.33, 254.21, 8, 252.3; 536/23.2

(56) References Cited

U.S. PATENT DOCUMENTS 5,229,285  7/1993  Kajiyama et al. .................... 435/189

FOREIGN PATENT DOCUMENTS 0 449 621   10/1991   (EP) .
0 524 488   1/1993    (EP) .
95 18853    7/1995    (WO) .

OTHER PUBLICATIONS

Wood, K.V. et al. "Complementary DNA coding click beetle luciferases can elicit bioluminescence of different colors." Science (May 1989), vol. 244, pp. 700–702.
Kajiyama, N. et al. "Thermostabilization of firefly luciferase by a single amino acid substitution at position 217." Biochemistry (Dec. 1993), vol. 32, No. 50, pp. 13795–13799.

Primary Examiner—Rebecca E. Prouty
(74) Attorney, Agent, or Firm—Nixon & Vanderhye PC

(57) ABSTRACT

Proteins are provided having luciferase activity with lower $K_m$ than wild-type luciferases by altering the amino acid residue at position 270 of the wild-type to an amino acid other than glutamate. Greater heat stability than wild-type luciferases while retaining the lower $K_m$ is provided by also replacing the glutamate equivalent to that at position 354 of *Photinus pyralis* luciferase or 356 of Luciola luciferases with an alternative amino acid, particularly lysine and/or the amino acid residue at 215 of *Photinus pyralis* and 217 of the Luciola species with a hydrophobic amino acid. DNA, vectors and cells that encode for and express the proteins are also provided as are test kits and reagents for carrying out luminescence assays using the proteins of the invention.

25 Claims, 4 Drawing Sheets

Plasmid pPW204

Plasmid pPW116

Figure 1:
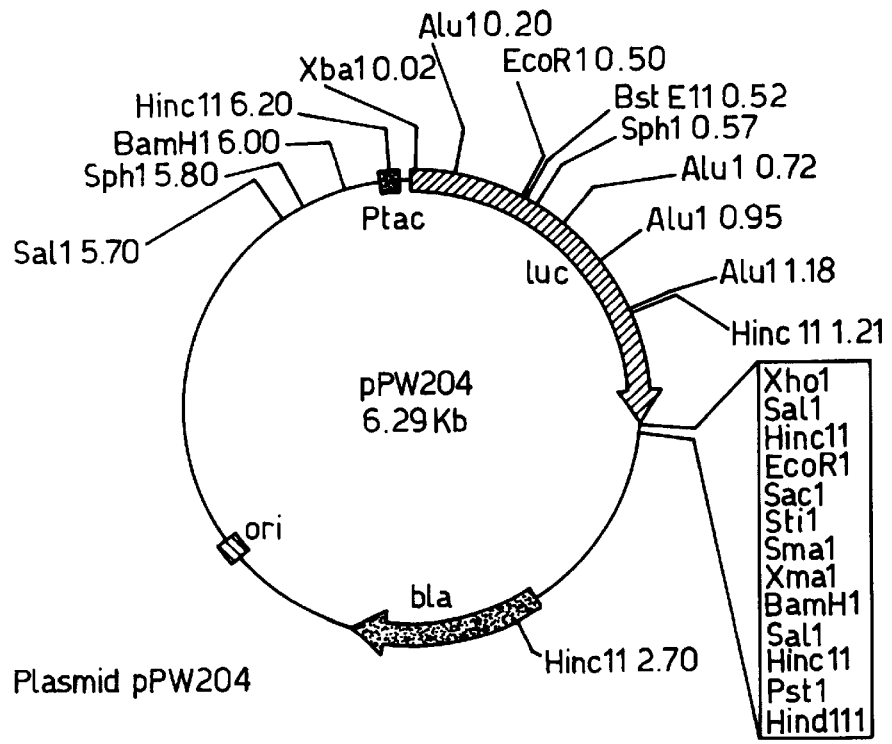

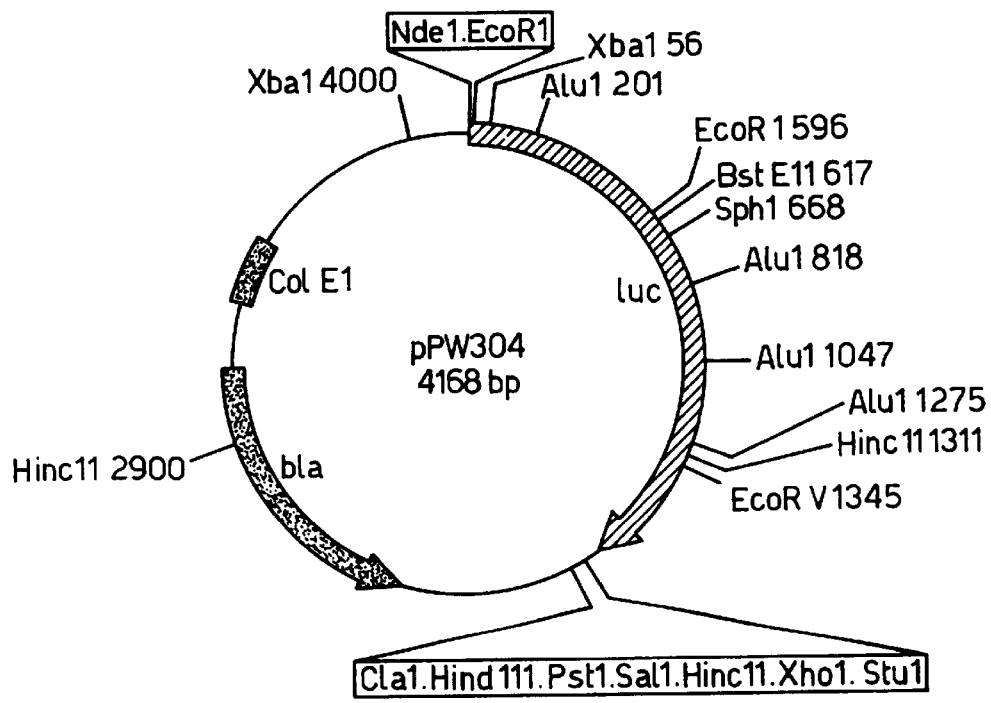
Plasmid pPW304
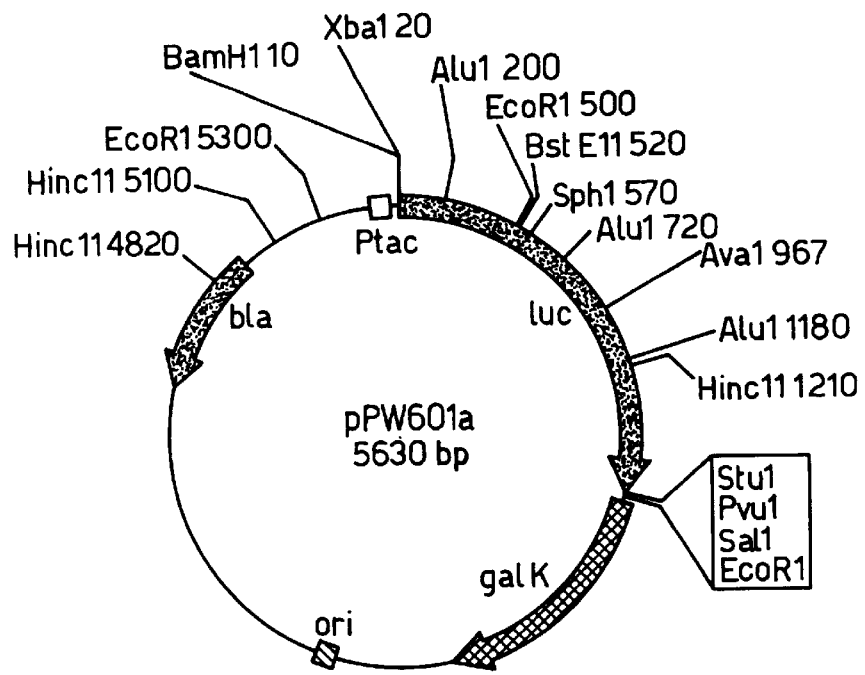

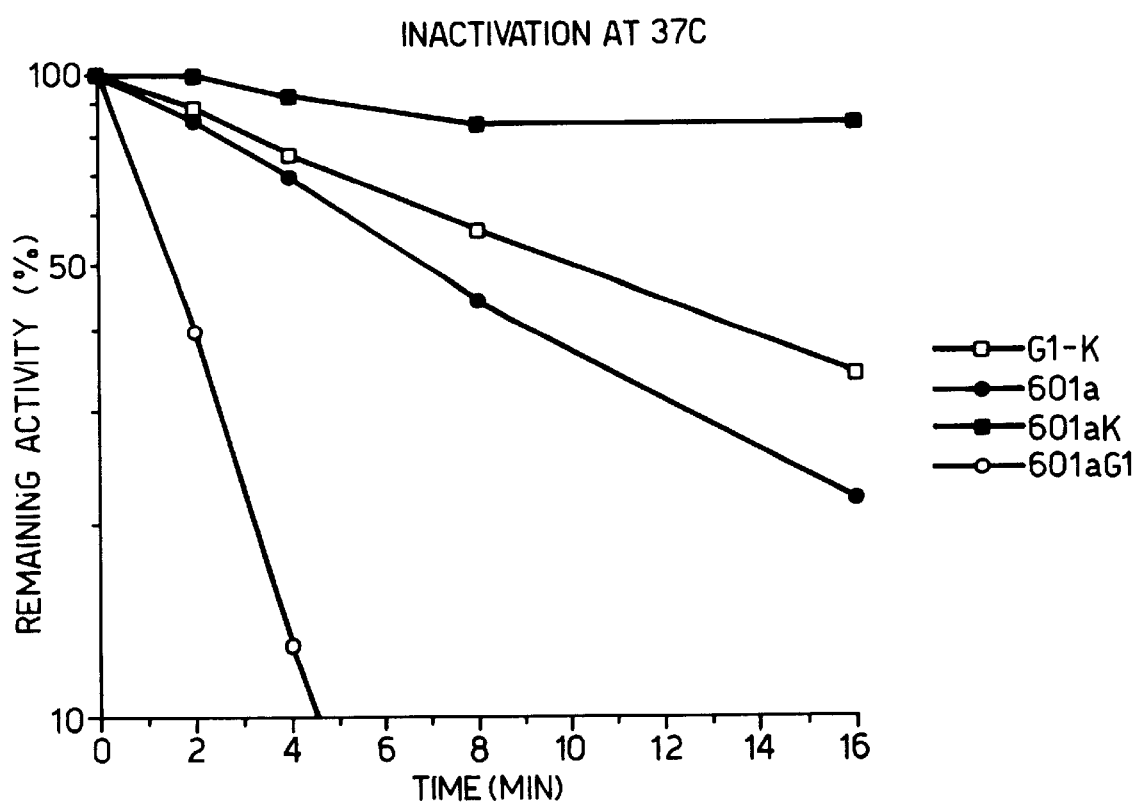

Fig. 6.

pT7-7

Contains T7 RNA polymerase promoter φ10 and the translation start site for the T7 gene 10 protein (T7 bp 22857 to 22972), inserted between the Pvu11 and the Cla1 sites of pT7-5. Unique restriction sites for creation of fusion proteins (after filling in 5' ends) are:
- Frame 0: EcoR1
- Frame 1: Nde1, Sma1, Cla1
- Frame 2: BamH1, Sal1, Hind111

Sac1 site of original polylinker removed by deletion.
Note the additional Xba1 site upstream of start codon.

Stan Tabor
Dept. of Biol. Chem.
Harvard Medical School
Boston, Mass. 02115

November 1987

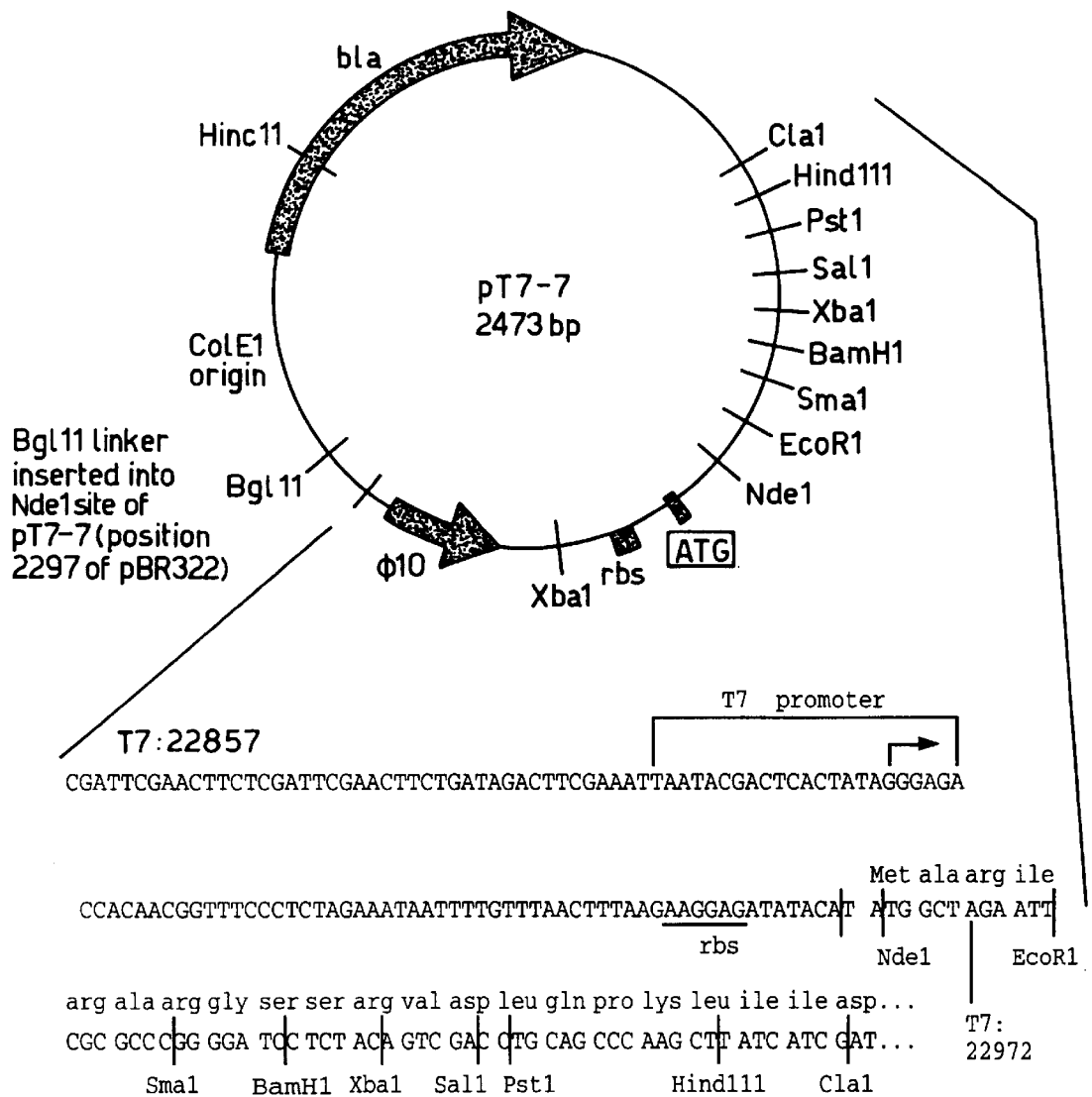

MUTANT LUCIFERASES

The present invention relates to novel proteins having luciferase activity and to DNA and vectors encoding for their expression. Particularly the present invention provides luciferases having lower $K_m$ for the substrate ATP than existing native and recombinant luciferases of wild and altered wild type.

Firefly luciferase catalyses the oxidation of luciferin in the presence of ATP, $Mg^{2+}$ and molecular oxygen with the resultant production of light. This reaction has a quantum yield of about 0.88 (see DeLuca & McElroy (1978) and Seliger & McElroy (1960)) and this light emitting property has led to its use in luminometric assays where ATP levels are being measured.

Luciferase is obtainable directly from bodies of fireflies or by expression from microorganisms including recombinant DNA constructs encoding for the enzyme. Significant species from which the enzyme may be obtained, or DNA encoding for it derived, are the Japanese GENJI and HEIKE fireflies *Luciola cruciata* and *Luciola lateralis,* the East European Firefly *Luciola mingrelica,* the North American firefly (*Photinus pyralis*) and the glow-worm and the European glow-worm *Lampyris noctiluca.*

The heat stability of wild and recombinant type luciferases is such that they lose activity quite rapidly when exposed to temperatures in excess of about 30° C., particularly over 35° C., and this renders the enzyme deficient when used at high ambient temperatures. It is known that Japanese firefly luciferase can be heat stabilised by mutating it at its position 217 to replace a threonine residue by an isoleucine residue (Kajiyama and Nakano (1993) Biochemistry 32 page 13795 to 13799); pH stability and specific activity also being increased.

Copending patent application GB 9405750.2 discloses an amino acid substitution that is capable of increasing the thermostability of inter alia, *Photinus pyralis* which can be used with the change at 217 to provide luciferase that is relatively heat stable at 50° C. or more.

The present invention relates to a further enhancement of the properties of luciferase enzymes, making them suitable for use in assays based upon the detection of adenosine triphosphate at relatively low levels. This enhancement is provided by changing the amino acid at the position corresponding to position 270 in the *Photinus pyralis* luciferase amino acid sequence whereby the Michaelis-Menten constant ($K_m$) of the enzyme is decreased as compared to a corresponding luciferase having wild-type sequence. This corresponds to amino acid 272 in *Luciola mingrelica, Luciola cruciata* and *Luciola lateralis.* It also corresponds to amino acid 270 in *Lampris Noctiluca.*

The present enhancement further provides luciferases that are characterised by the ability to oxidise D-luciferin with light emission of a different wavelength to that of wild-type luciferase, thus allowing them to be used as specific labels in binding assays wherein the wavelength of light emitted is characteristic of a particular labelled material being present, or allows DNA encoding for the luciferases to be used as a reporter DNA for genetically engineered cells and cells derived therefrom.

Thus in the first aspect of the present invention there is provided a protein having luciferase activity and having over 60% homology of amino acid sequence with that of *Photinus pyralis, Luciola mingrelica, Luciola cruciata* or *Luciola lateralis* characterised in that the amino acid residue corresponding to residue 270 of *Photinus pyralis* luciferase and residue 272 of *Luciola mingrelica, Luciola cruciata* and *Luciola lateralis* luciferase is an amino acid other than glutamate. Preferably is characterised in that it comprises a conserved amino acid sequence F(1)XE(2)FL wherein (1) is D or E, (2) is T or L and X is the amino acid other than glutamate; F, E, L, D and T each relating to the corresponding amino acid as provided for by the single letter amino acid code.

The preferred amino acid X so far determined is lysine, or an analogue or modification thereof. Other preferred amino acids include arginine, glutamine and alanine.

In still more preferred forms of the present invention the protein of the invention also has the amino acid at the position corresponding to amino acid 217 of the Luciola firefly luciferases or 215 of *Photinus pyralis* changed to a hydrophobic amino acid, preferably to isoleucine, leucine or valine or analogue or these and/or has the amino acid at the position corresponding to amino acid 356 of the Luciola firefly luciferase or 354 of *Photinus pyralis* changed to an amino acid other than glutamate, particularly to lysine, arginine, leucine, isoleucine or histidine or analogues or modifications of these.

In a second aspect of the invention there is provided DNA encoding for the protein of the invention and in a third aspect there is provided a vector, particularly a plasmid, comprising a luc gene (the gene encoding for luciferase) in such a form as to be capable of expressing the protein of the invention. Such forms are those where the vector includes DNA sequences capable of controlling the expression of the protein of the invention such that when incorporated into a microorganism host cell the protein may readily be expressed as required, if necessary by addition of suitable inducers.

The luc genes for *Photinus pyralis, Luciola mingrelica, Luciola cruciata* and *Luciola lateralis* are all known and isolatable by standard molecular biology techniques. This is also the case for *Lampris noctiluca. Photinus pyralis* luc gene is commercially available from Promega as the plasmid pGEM-luc. Thus convenient methods and sources for deriving starting material for production of DNA of the invention are (i) use of naturally occurring firefly genomic DNA and amplifying the luc gene from it using eg, PCR, (ii) pGEM and (iii) pGLf37 plasmid of Kajiyama and Nakano. Further genes encoding for proteins having luciferase activity, ie the activity of oxidising luciferin with the emission of light, will also be suitable sources for starting material for obtaining a DNA, and ultimately through gene expression, a protein of the invention.

Suitable vectors for use in manipulating wild type or other luc gene DNA in order to produce the DNA of the invention will be any vector in which the DNA can be contained within while alteration of the naturally occurring glutamate to an alternative amino acid is carried out. For chemically induced mutagenesis, eg using agents such as hydroxylamine, this is not particularly critical and many suitable vectors will occur to those skilled in the art that will allow easy manipulation of the gene before and after the mutagenic process. It may be preferred to specifically mutate the luc gene at the glutamate and thus a site directed mutagenesis operation will be required. Such operations may be most easily carried out in vectors and these will be well known to those skilled in the art.

For expression of luc genes of wild and known type, and those of the present invention suitable vectors include pKK223-3, pDR540 (available from Boehringer Mannheim) and pT7-7; the first two having the tac promoter under control of the lactose repressor allowing expression to be induced by presence of isopropyl-thiogalactoside (IPTG).

pT7-7 allows control by the T7-RNA polymerase promoter and thus provides the basis for a very high level of gene expression in *E. coli* cells containing T7 RNA polymerase. Of these vectors expression is found to be highest when the luc genes are inserted into the pT7-7 vector.

Expression of luciferase from a luc gene inserted into pKK223-3 and pDR540 results in the expression of wild-type N-terminal sequence luciferase whilst expression from a luc gene inserted into pT7-7 results in synthesis of a fusion protein with extra N-terminal amino acids A-R-I-Q (SEQ ID NO: 6). The ribosome binding site and start codon of the luc gene in each of the respective vectors with the luc gene present (named constructs pPW204, pPW116 and pPW304) are shown in Table 1 of the Examples. pPW601a referred to below is derived by removing the unique Xho I site pPW116.

A third aspect of the present invention provides cells capable of expressing the proteins of the invention; methods for producing such proteins using these cells and test kits and reagents comprising the proteins of the invention. Also provided are assay methods wherein ATP is measured using luciferin/luciferase reagents, as is well known in the art, characterised in that the luciferase is a protein of the invention. Luciferase preparations of the invention are relatively low in $K_m$ with respect to the corresponding wild type and recombinant luciferases, and preferred double and triple change luciferases (ie 215; 270; 354 changed Photinus or 217; 272; 356 changed Luciola, or 215; 270; 354 changed *L. noctiluca* also have the property of relative thermostability at 30–70° C., particularly 37–60° C., and especially 40–50° C. Thus the present invention has been established as not preventing the thermostability enhancements of other contemporaneous and previous work by the present inventors and others from being used.

Any cell capable of expressing heterologous protein using DNA sequences in its DNA, or in vectors such as plasmids contained in the cell, may be used to express the proteins of the invention. Typical of such cells will be yeast and bacterial cells such as *Saccharomyces cerevisiae* and *Escherichia coli* cells, but many other host organisms suitable for the purpose of protein expression will occur to those skilled in the art.

The protein may be expressed as a protein of similar structure to native and known recombinant luciferases, or may be expressed as a fusion or conjugate of such proteins with other amino acids peptides, proteins or other chemical entities, eg the A-R-I-Q (SEQ ID NO: 6) sequence above.

It will be realised by those skilled in the art that certain hosts may have particular codon preferences, eg bacteria in some cases use different codons to yeast, and thus the DNA incorporated into such a host may advantageously be altered to provide a degenerate codon for a given amino acid that will give more favourable expression in that host. Such degenerate DNAs are of course included in the scope of the DNA of the invention.

*E. coli* BL21 (DE3) is one suitable host and has the T7 RNA polymerase integrated stably into its chromosome under control of the inducible lacUV5 promoter and is thus compatible with pT7-7 derived constructs.

*E. coli* B strains like BL21 lack the lon protease and the ompT outer membrane protease. These deficiencies can help to stabilise the expression and accumulation of foreign proteins in *E. coli*. Assays of crude extracts of *E. coli* BL21 (DE3) containing each of the three expression constructs described above indicated that the highest levels of expression of luciferase were obtained from cells containing the construct pPW304 (see Table 2). Other suitable cell lines, such as that of the *E. coli* JM109 cells used in the Examples below will occur to those skilled in the art.

The proteins, DNA, vectors and cells of the invention will now be described by way of illustration only by reference to the following non-limiting Examples, Figures, Tables and Sequence listing. Further proteins, conjugates of proteins, DNA, vectors and cells, and assays and test kits incorporating any of the above will occur to those skilled in the art in the light of these.

FIGURES

FIG. 1: shows a restriction map of plasmid pPW204 derived from pKK223-3 by insertion of a luc gene as described in the Examples below.

Figure 2:
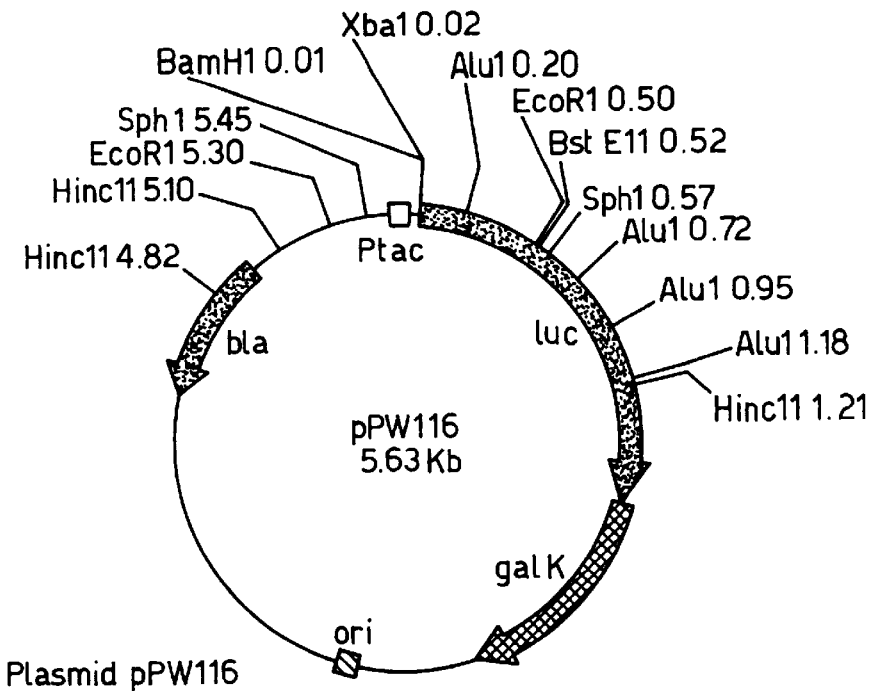

FIG. 2: shows a restriction map of plasmid pPW116 derived from pDR540 by insertion of a luc gene as described in the Examples below.

FIG. 3: shows a restriction map of plasmid pPW304 derived from pT7-7 by insertion of a luc gene as described in the Examples below.

FIG. 4: shows a restriction map of plasmid pPW601a derived from pDR540 and BamH1/Sst1 fragment from pGEM-luc with the Xho site removed.

FIG. 5: shows a graph of heat inactivation of recombinant wild-type Photinus luciferases (Sigma), $K_m$ changed luciferase of the invention, the thermostable 354 lysine mutant provided by copending GB 9405750.2 and $K_m$/354 lysine double mutant of the present invention incubated at a given temperature for 16 minutes as described in the Examples below.

FIG. 6: shows a restriction map of pT7-7 after Tabor (SEQ ID NO: 12 and SEQ ID NO: 13).

SEQUENCE LISTING

The sequence listing provided at the end of this specification describes DNA and amino acid sequences as follows:

SEQ ID No 1: shows the DNA sequence of a DNA encoding for luciferase of the invention wherein the *Photinus pyralis* wild-type codon at 811 to 813 is mutated; for lysine only the base at 811 is mutated to an A. It also shows the position for introducing thermostability at 1063–65.

SEQ ID No 2: shows the amino acid sequence of a protein of the invention wherein the *Photinus pyralis* wild-type amino acid 270 glutamate has been changed to a residue Xaa other than glutamate.

SEQ ID No 3: shows the sequence of the oligonucleotide used for the SDM mutation of pPW601a to give a lysine instead of glutamate at position 270.

SEQ ID No 4: shows the amino acid sequence of a protein of the invention wherein the *Photinus pyralis* wild-type amino acid 270 glutamate has been changed to lysine and the 354 amino acid changed to lysine.

SEQ ID No 5: shows the sequence of the oligonucleotide used for the SDM mutation of pPW601a to give a lysine instead of glutamate at position 354.

EXAMPLES

Example 1: Production of Plasmids Containing DNA of the Invention

Plasmids pKK223-3 and pDR540 were obtained form Boehringer Mannheim; pDR540 is also available from Pharmacia Biotech St Albans UK. Phagemid pBluescript II SK(+) was obtained from Stratagene La Jolla, USA. *E. coli* strain BL21 (DE3) was used for the expression of luciferase from pT7-7 derived plasmids and *E. coli* strain JM109 (4) was used in all cloning experiments and for the expression of luciferase from pDR540 derived plasmids.

Plasmid pT7-7 (see Current protocols in Molecular Biology Vol II Section 16.2.1) was obtained from Stan Tabor, Dept of Biol Chem, Harvard Medical School, Boston, Mass. 02115 and (as shown in FIG. 6) contains T7 RNA polymerase promoter Ø10 and the translation start site for the T7 gene 10 protein (T7 bp 22857 to 22972) inserted between the PvuII and ClaI sites of pT7-5. Unique restriction sites for creation of fusion proteins (after filling in 5' ends) are Frame 0: EcoR1; Frame 1: NdcI, SmaI, ClaI; Frame 2: BamHI, SalI, HindIII. SacI site of the original polylinker is removed by deletion and an additional XbaI site is provided upstream of the start codon.

As stated in the preamble to the Figures, pPW204 was derived from pKK223-3; pPW116 was derived from pDR540; pPW304 derived from pT7-7; each by insertion of a luc gene derived from Promega pGEM-luc using standard restriction endonuclease and ligation techniques while pPW601 was created by cloning the luc gene and BamH1/Sst1 fragment from pGEM-luc into pDR540 and pPW601a as derived by removing the unique Xho I site in the polylinker of the plasmid. pPW601a contains a unique recognition site for Ava I which simplifies the SDM procedure for luciferase amino acid 354 changes.

For production of pPW304, pT7-7 is digested with EcoRI, the ends filled using Klenow fragment, the product digested with SalI and the DNA gel purified; pGEM-luc is digested with Bam HI, the overhangs produced digested with MBN, the product digested with SalI and the 1 Kb fragment produced purified and ligated to the purified pT7-7 DNA.

Transformation of plasmids into BMH 71-18 mut S cells was carried out using a Bio-Rad Gene Pulser version 2-89. For production of pPW601 clones harvested cells and purified mixed plasmid pool containing mutated and parental plasmids were provided and secondary restriction digest with AvaI was carried out before transformation into *E. coli* JM109 cells. These cells were plated on selective media (LB agar+50 µg/ml ampicillin) and clones screened by purifying their plasmid DNA and analysing for the desired change. Plasmid DNA was purified using alkaline lysis (Birnboim & Doly (1979) Nucleic Acids Research 7, p1513).

Relative levels of expression of luciferase from each of the constructs pPW204, pPW116 and pPW304 are 0.1:0.5:1.0 from *E. coli* BL21 (DE3). Cells were grown in LB at 37° C. to an OD 600 of 0.3 then induced with IPTG and growth allowed to continue for 4 hours after which crude extract was prepared and luciferase activity measured.

Partial purification of luciferases was carried out on *E. coli* JM109 cells harvested in the early stationary phase then resuspended in 50 mM Tris HCl pH 8.0 containing 50 mM KCl, 0.5 mM dithreitol and 1 mM EDTA (Buffer A). Cells were broken up by disruption in a MSE soniprep (amplitude 14µ) and the lysate centrifuged at 30000×g for 1 hour. The supernatant of the crude extract was then subjected to fractionation with ammonium sulphate and the fraction precipitated between 35% and 55% saturation contained luciferase activity and was dissolved in Buffer A and dialysed overnight against 500 ml of 50 mM Tris-HCl buffer pH8.0 containing 0.4 mM DTT (Buffer B).

Full purification of luciferases was carried out by applying the precipitated and dialysed enzyme to a Mono Q (HR10/10) anion exchange column and eluting that with a linear gradient of 0–200 mM NaCl in Buffer B (flow-rate 4 ml/minute; 2 ml fractions). Peak fractions containing luciferase activity were made to 50% glycerol (v/v) and stored at −20° C.

Firefly luciferase (prepared from a crystalline suspension, Cat No L9009) and coenzyme A and ATP were obtained from Sigma Chemical Co. Beetle luciferin potassium salt was obtained from Promega Corporation, Madison Wis., USA. Cell extracts were prepared as described in the Promega technical bulletin No 101. Aliquots of *E. coli* cultures were lysed in cell culture lysis reagent (25 mM Tris-phosphate, pH7.8, 2 mM DTT, 2 mM EDTA, 10% glycerol, 1% Triton X-100, 2.5 mg/ml BSA, 1.25 mg/ml lysozyme) for 10 minutes at room temperature, centrifuged at 16000 g for 2 minutes and then stored on ice prior to assay.

Luciferase activity of cell lines was assayed by monitoring bioluminescence emitted by colonies by transferring these to nylon filters (Hybond N, Amersham) and then soaking the filters with 0.5 mM luciferin in 100 mM sodium citrate buffer pH5.0 (Wood & DeLuca, (1987) Anal Biochem 161 p501–507) at room temperature. Luciferase assays in vitro were performed at 21° C. using 100 µl of assay buffer (20 mM Tricine pH7.8 containing 1 mM MgSO$_4$, 0.1 mM EDTA, 33.3 mM DTT, 0.27 mM conenzyme A, 0.47 mM D-luciferin, 0.53 mM ATP and 1 to 5 µl of sample). The final pH of the assay cocktail was 7.8 and light measurements were made with a BioOrbit 1250 luminometer or in microtitre plates using a labsystems luminoskan RS plate luminometer.

Protein was determined by the method of Bradford (1976) Anal. Biochem. 72 p248–254 using BSA as standard. For production of non-specific chemical mutations of DNA, plasmids containing luc genes were treated according to the method of Kironde et al (1989) Biochem. J. 259, p421–426 using 0.8M hydroxylamine, 1 mM EDTA in 0.1 mM sodium phosphate pH6.0 for 2 hours at 65° C.

The $K_m$ mutant was initially generated by hydroxylamine induced mutagenesis of the luc gene within pPW304 to provide plasmid 304 G1 bearing a single base change in the DNA sequence at 811 of SEQ ID No 1 resulting in an amino acid glutamate change to lysine at position 270. A 1.1 kb DNA fragment (BstE II/Stu I) was cloned from pPW304 and used to replace the corresponding fragment in pP601a to

TABLE 1

Ribosome binding sites (underlined) and start codons in the expression constructs pPW304(SEQ ID NO:7) <u>AAGGAG</u>ATATACAT ATG* CGT AGA ATT CAA ATG pPW116(SEQ ID NO:8) <u>AGGAAAC</u><u>AGGA</u>TCCA ATG* pPW204(SEQ ID NO:9) <u>AGGAAAC</u>AGCAA ATG* form pPW601G1, thus providing a luc gene encoding for luciferase without the four extra amino acids encoded by pPW304 (M not included from M-A-R-I-Q).

This mutagenised plasmid was desalted on a G60 DNA grade Nick column (Pharmacia) followed by transformation into *E. coli* BL21 (DE3). Luciferase expressed from this showed an identical low $K_m$ phenotype to that of the original mutant.

Double stranded DNA sequencing was performed by the dideoxy chain termination method of Sanger et al (1977) Proc. Nat. Acad. Sci. (USA) 74, 5463–5467 using [alpha-$^{32}$P]dATP and electrophoresis in 8M urea (6% wt/vol) polyacrylamide gels. Automatic sequencing was also undertaken using a DNA model 373A automated sequencer (Applied Biosystems).

Assay for determining the $K_m$ value of this luciferase with respect to ATP was carried out at 21° C. with 100 µl of assay buffer (20 mM tricine pH7.8 containing 1.0 mM $MgSO_4$, 0.1 mM EDTA, 33 mM dithiothreitol, 270 µM coenzyme A, 470 µM D-luciferin and 6.25 to 400 µM ATP) using a luminometer to measure cpm.

The $K_m$ value for 601a-recombinant wild-type was determined to be 66.1 µM (s.e. 4.1); for 601aK (thermostable mutant 354 lysine) was 61.3 (s.e. 4.7) and for 601aG1 (270 lysine $K_m$ change) was 28.7 (s.e. 0.9) thus illustrating that the 270 change more than halves the ATP concentration for which the enzyme is optimised.

The effect of the 270 change on the thermostability of luciferase is negative, with $t_{1/2}$ activity being reached after only 2 minutes as compared to wild-type at 7 minutes, both at 37° C.; however at 30° C. the specific activity of 270 is greater than wild-type.

Example 2: Preparation of 'double mutant' 270K: 354K *Photinus pyralis* luciferase In order to offset the reduced thermostability of the 270 change luciferase, a double change luciferase was provided by using site directed mutagenesis to engineer the lysine change at 354 into the 270-lysine luciferases encoding DNA and plasmid described in Example 1. This involved mutation using specifically designed oligonucleotides to convert pPW601aG1 to pPW601a to G1K.

The oligonucleotide used to generate the 354 lysine change by SDM was CATCCCCCTTGGGTGTAATCAG (SEQ ID No 5) with the underlined T being the mismatch.

The site directed mutagenesis required to convert the glutamate 354 of pPW601aE270K, and where required for direct synthesis of 270 mutant from pPW601a, to desired amino acids is carried out using the following protocol with oligonucleotides designed as required.

Site Directed Mutagenesis Protocol: Plasmid selected is denatured and annealed with selection and mutagenic oligonucleotides for the desired change. The mutant DNA strand is synthesised and ligated and the whole primary restriction digested with a restriction endonuclease. Oligonucleotide primers for sequencing and SDM were synthesised using an Applied Biosystems model 380A DNA synthesiser. DNA oligonucleotide primers were designed to destroy either a unique Ava I site within the luc gene or the unique ScaI site within the gene for β-lactamase; the presence of these sites being used to select against plasmids that had not undergone mutagenesis. Precise protocols were as described in the Transformer™ Site-Directed Mutagenesis Kit (Version 2.0) sold by Clontech Laboratories Inc (US) catalog No K1600-1.

The restriction map for pPW601 derived from pDR540 and cloned luc gene is shown as FIG. 4. Site directed mutagenesis was carried out as described above and in the Clontech instructions such as to convert the wild-type Photinus luc gene inserted therein into a sequence as shown in SEQ ID No 1 with expressed protein of amino acid sequence modified at position 270 as shown as Xaa in SEQ ID No 2 to Lysine.

$K_m$ studies were carried out as described in Example 1 while heat inactivation studies were carried out using crude extracts at 37° C. in lysis buffer (25 mM Tris phosphate pH7.8, 2 mM DTT. 2 mM EDTA, 10% glycerol and 1% Triton X-100) at various time points aliquots of enzyme were removed and assayed as described above (with 530 µM ATP). The remaining activity was plotted against time.

The $K_m$ value for 601aG1K, the double change of this example, was found to be 25.2 µM (s.e. 1.5) being again less than half that of the corresponding 354 lysine mutant and the wild-type luciferase.

The $t_{1/2}$ value, the time after which the activity of the luciferase is reduced on continuous heating to 50% of its initial value, was found to be as follows:

| | | |
|---|---|---|
| 601a | (recombinant wild-type) | $t_{1/2}$ reached after 7.0 minutes |
| 601aG1 | (270 $K_m$ change) | $t_{1/2}$ reached after 1.75 minutes |
| 601aK | (354 thermostable change) | $t_{1/2}$ reached after >35 minutes |
| 601aG1K | (270 + 354 change) | $t_{1/2}$ reached after 10.5 minutes |

The above data is included below (plus other data) along with Km values.

| | Km ATP | $t_{1/2}$ 37° C. (min) |
|---|---|---|
| recombinant wild type | 66.1 | 7.0 |
| E270K | 28.7 | 1.75 |
| E354K | 61.3 | >35 |
| E270K + E354K | 25.2 | 10.5 |
| E270R | 32.0 | 1.75 |
| E270Q | 44.0 | 1.75 |
| E270A | 37.0 | 1.75 |

What is claimed is:

1. An isolated mutant luciferase protein having luciferase activity, which has over 60% amino acid sequence homology to the luciferase from *Photinus pyralis, Luciola mingrelica, Luciola cruciata* or *Luciola lateralis* and which includes the amino acid sequence F(1)XE(2)FL (SEQ ID NO: 6), where (1) is D or E, (2) is T or L and X is an amino acid other than glutamate and is at a position corresponding to amino acid residue 270 of *Photinus pyralis* luciferase as shown in SEQ ID NO: 2.

2. A protein as claimed in claim 1 wherein it further comprises an amino acid sequence TPXGDDKPGA (SEQ ID NO. 7) wherein X is an amino acid residue other than glutamate.

3. A protein as claimed in claim 1, wherein the amino acid residue X is lysine.

4. A protein as claimed in claim 1 wherein the amino acid residue corresponding to residue 215 of *Photinus pyralis* luciferase is a hydrophobic amino acid.

5. A protein as claimed in claim 4 wherein the residue corresponding to residue 215 of *Photinus pyralis* luciferase is one of isoleucine, leucine or valine.

6. A protein as claimed in claim 1 wherein the amino acid residue corresponding to residue 354 of *Photinus pyralis* luciferase is an amino acid other than glutamate.

7. A protein of claim 6 wherein the residue corresponding to residue 354 of *Photinus pyralis* luciferase is one of lysine, arginine, leucine, isoleucine or histidine.

8. An isolated DNA encoding for a protein as claimed in claim 1.

9. An isolated DNA as claimed in claim 8 comprising a nucleotide sequence as described in SEQ ID No 1 wherein nucleotide residues 811–813 form a codon encoding an amino acid other than glutamate.

10. An isolated DNA as claimed in claim 9 wherein the codon encodes lysine.

11. A vector comprising a luc gene encoding a protein as claimed in claim 1.

12. A vector as claimed in claim 11 obtainable by treating a vector containing a wild-type or recombinant luc gene by site directed mutagenesis to change the codon responsible for encoding the glutamate at position 270 of *Photalis pyralis* luciferase to an alternative amino acid.

13. A vector as claimed in claim 12 wherein the alternative amino acid is lysine.

14. A vector as claimed in claim 11 selected from pKK223-3, pDR540 and pT7-7 into which said luc gene has been ligated.

15. A cell transformed with a DNA or a vector capable of expressing a protein as claimed in claim 1.

16. A cell as claimed in claim 15 which is an *E. coli* or a *S. cerevisiae* cell.

17. A test kit for performance of an assay through measurement of ATP wherein the kit comprises a protein as claimed in claim 1.

18. An assay method wherein ATP is measured using luciferin and luciferase to generate light the quantity of which is related to the amount of ATP wherein the luciferase is a protein as claimed in claim 1.

19. An assay method as claimed in claim 18 wherein the assay is carried out at a temperature of from 30° C. to 70° C.

20. An assay method as claimed in claim 18 wherein the assay is carried out at a temperature of from 37° C. to 60° C.

21. An assay method as claimed in claim 18 wherein the assay is carried out at a temperature of from 40° C. to 50° C.

22. A protein comprising an amino acid sequence as described in SEQ ID No 2 wherein Xaa is chosen from arginine, glutamine and alanine.

23. A mutant luciferase protein of claim 1 wherein said luciferase protein is a firefly or a glow worm luciferase.

24. A mutated luciferase of claim 1 wherein said luciferase is a Photinus luciferase.

25. A mutant luciferase protein as claimed in claim 1 wherein said luciferase has a $K_m$ to the substrate ATP which is lower than that of the corresponding wild type luciferase.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 1722 base pairs (B) TYPE: nucleic acid
         (C) STRANDEDNESS: double
         (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
         (A) ORGANISM: Photinus pyralis (ix) FEATURE:
         (A) NAME/KEY: CDS
         (B) LOCATION: 4..1653

(ix) FEATURE:
         (A) NAME/KEY: misc_difference
         (B) LOCATION: replace(811..813, "")

(xi) SEQUENCE DESCRIPTION: SEQ ID NO: 1:

```
CAAATGGAAG ACGCCAAAAA CATAAAGAAA GGCCCGGCGC CATTCTATCC TCTAGAGGAT    60
GGAACCGCTG GAGAGCAACT GCATAAGGCT ATGAAGAGAT ACGCCCTGGT TCCTGGAACA   120
ATTGCTTTTA CAGATGCACA TATCGAGGTG AACATCACGT ACGCGGAATA CTTCGAAATG   180
TCCGTTCGGT TGGCAGAAGC TATGAAACGA TATGGGCTGA ATACAAATCA CAGAATCGTC   240
GTATGCAGTG AAAACTCTCT TCAATTCTTT ATGCCGGTGT TGGGCGCGTT ATTTATCGGA   300
GTTGCAGTTG CGCCCGCGAA CGACATTTAT AATGAACGTG AATTGCTCAA CAGTATGAAC   360
ATTTCGCAGC CTACCGTAGT GTTTGTTTCC AAAAAGGGGT TGCAAAAAAT TTTGAACGTG   420
CAAAAAAAAT TACCAATAAT CCAGAAAATT ATTATCATGG ATTCTAAAAC GGATTACCAG   480
GGATTTCAGT CGATGTACAC GTTCGTCACA TCTCATCTAC CTCCCGGTTT AATGAATAC    540
GATTTTGTAC CAGAGTCCTT TGATCGTGAC AAAACAATTG CACTGATAAT GAATTCCTCT   600
GGATCTACTG GGTTACCTAA GGGTGTGGCC CTTCCGCATA GAACTGCCTG CGTCAGATTC   660
TCGCATGCCA GAGATCCTAT TTTTGGCAAT CAAATCATTC CGGATACTGC GATTTTAAGT   720
GTTGTTCCAT TCCATCACGG TTTTGGAATG TTTACTACAC TCGGATATTT GATATGTGGA   780
TTTCGAGTCG TCTTAATGTA TAGATTTGAA NNNGAGCTGT TTTTACGATC CCTTCAGGAT   840
TACAAAATTC AAAGTGCGTT GCTAGTACCA ACCCTATTTT CATTCTTCGC CAAAAGCACT   900
CTGATTGACA AATACGATTT ATCTAATTTA CACGAAATTG CTTCTGGGGG CGCACCTCTT   960
TCGAAAGAAG TCGGGGAAGC GGTTGCAAAA CGCTTCCATC TTCCAGGGAT ACGACAAGGA  1020
TATGGGCTCA CTGAGACTAC ATCAGCTATT CTGATTACAC CCNNNGGGGA TGATAAACCG  1080
GGCGCGGTCG GTAAAGTTGT TCCATTTTTT GAAGCGAAGG TTGTGGATCT GGATACCGGG  1140
AAAACGCTGG GCGTTAATCA GAGAGGCGAA TTATGTGTCA GAGGACCTAT GATTATGTCC  1200
GGTTATGTAA CAATCCGGA AGCGACCAAC GCCTTGATTG ACAAGGATGG ATGGCTACAT   1260
TCTGGAGACA TAGCTTACTG GGACGAAGAC GAACACTTCT TCATAGTTGA CCGCTTGAAG  1320
TCTTTAATTA AATACAAAGG ATATCAGGTG GCCCCCGCTG AATTGGAATC GATATTGTTA  1380
CAACACCCCA ACATCTTCGA CGCGGGCGTG GCAGGTCTTC CCGACGATGA CGCCGGTGAA  1440
CTTCCCGCCG CCGTTGTTGT TTTGGAGCAC GGAAAGACGA TGACGGAAAA AGAGATCGTG  1500
GATTACGTCG CCAGTCAAGT AACAACCGCG AAAAAGTTGC GCGGAGGAGT TGTGTTTGTG  1560
GACGAAGTAC CGAAAGGTCT TACCGGAAAA CTCGACGCAA GAAAAATCAG AGAGATCCTC  1620
ATAAAGGCCA AGAAGGGCGG AAAGTCCAAA TTGTAAAATG TAACTGTATT CAGCGATGAC  1680
```

-continued

```
GAAATTCTTA GCTATTGTAA TCCTCCGAGG CCTCGAGGTC GA                    1722
```

(2) INFORMATION FOR SEQ ID NO: 2:

(i) SEQUENCE CHARACTERISTICS:
       (A) LENGTH: 550 amino acids
       (B) TYPE: amino acid
       (C) STRANDEDNESS: single
       (D) TOPOLOGY: unknown (ii) MOLECULE TYPE: protein (iii) HYPOTHETICAL: NO (vi) ORIGINAL SOURCE:
       (A) ORGANISM: Photinus pyralis (ix) FEATURE:
       (A) NAME/KEY: Modified-site
       (B) LOCATION: 270

(xi) SEQUENCE DESCRIPTION: SEQ ID NO: 2:

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Xaa Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
```

```
                       290                 295                 300
Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
                530                 535                 540

Gly Gly Lys Ser Lys Leu
545                 550

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (vi) ORIGINAL SOURCE:
        (A) ORGANISM: Photinus pyralis (ix) FEATURE:
        (A) NAME/KEY: misc_difference
        (B) LOCATION: replace(10, "")

(xi) SEQUENCE DESCRIPTION: SEQ ID NO: 3:

GTATAGATTT GAAAAAGAGC TGTTTTTACG                                        30

(2) INFORMATION FOR SEQ ID NO: 4:

(i) SEQUENCE CHARACTERISTICS:
        (A) LENGTH: 550 amino acids
```

(B) TYPE: amino acid
        (C) STRANDEDNESS: single
        (D) TOPOLOGY: unknown (ii) MOLECULE TYPE: protein (iii) HYPOTHETICAL: NO (vi) ORIGINAL SOURCE:
        (A) ORGANISM: Photinus pyralis (ix) FEATURE:
        (A) NAME/KEY: Modified-site
        (B) LOCATION: 354

(ix) FEATURE:
        (A) NAME/KEY: Modified-site
        (B) LOCATION: 270

(xi) SEQUENCE DESCRIPTION: SEQ ID NO: 4:

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
             20                  25                  30

Tyr Ala Leu Val Pro Gly Thr Ile Ala Phe Thr Asp Ala His Ile Glu
         35                  40                  45

Val Asn Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
65                   70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
            115                 120                 125

Ser Lys Lys Gly Leu Gln Lys Ile Leu Asn Val Gln Lys Lys Leu Pro
        130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Leu Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Lys Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser

```
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Lys Gly Asp Asp Lys Pro Gly Ala Val Gly Lys Val Val Pro Phe
                355                 360                 365
Phe Glu Ala Lys Val Val Asp Leu Asp Thr Gly Lys Thr Leu Gly Val
                370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
                435                 440                 445
Val Ala Pro Ala Glu Leu Glu Ser Ile Leu Leu Gln His Pro Asn Ile
                450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
                515                 520                 525
Lys Leu Asp Ala Arg Lys Ile Arg Glu Ile Leu Ile Lys Ala Lys Lys
                530                 535                 540
Gly Gly Lys Ser Lys Leu
545                 550

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: cDNA to mRNA (iii) HYPOTHETICAL: NO (vi) ORIGINAL SOURCE:
        (A) ORGANISM: Photinus pyralis (ix) FEATURE:
        (A) NAME/KEY: misc_difference
        (B) LOCATION: replace(10, "")

(xi) SEQUENCE DESCRIPTION: SEQ ID NO: 5:

CATCCCCCTT GGGTGTAATC AG                                                    22

(2) INFORMATION FOR SEQ ID NO: 6:

(i) SEQUENCE CHARACTERISTICS:
        (A) LENGTH: 4 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 6:

Ala Arg Ile Gln
1

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

AAGGAGATAT ACATATGCGT AGAATTCAAA TG                                      32

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

AGGAAACAGG ATCCAATG                                                      18

(2) INFORMATION FOR SEQ ID NO: 9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

AGGAAACAGC AAATG                                                         15

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Phe Xaa Xaa Glu Xaa Phe Leu
1               5

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Thr Pro Xaa Gly Asp Asp Lys Pro Gly Ala
1               5                   10
```

(2) INFORMATION FOR SEQ ID NO: 12:

(i) SEQUENCE CHARACTERISTICS:
        (A) LENGTH: 186 base pairs
        (B) TYPE: nucleic acid
        (C) STRANDEDNESS: both
        (D) TOPOLOGY: both (ii) MOLECULE TYPE: other nucleic acid
        (A) DESCRIPTION: /desc = "PLASMID"

(ix) FEATURE:
        (A) NAME/KEY: CDS
        (B) LOCATION: 124..186

(xi) SEQUENCE DESCRIPTION: SEQ ID NO: 12:

```
CGATTCGAAC TTCTCGATTC GAACTTCTGA TAGACTTCGA AATTAATACG ACTCACTATA       60

GGGAGACCAC AACGGTTTCC CTCTAGAAAT AATTTTGTTT AACTTTAAGA AGGAGATATA      120

CAT ATG GCT AGA ATT CGC GCC CGG GGA TCC TCT ACA GTC GAC CTG CAG       168
    Met Ala Arg Ile Arg Ala Arg Gly Ser Ser Thr Val Asp Leu Gln
        1               5                  10                  15

CCC AAG CTT ATC ATC GAT                                                186
Pro Lys Leu Ile Ile Asp
                20
```

(2) INFORMATION FOR SEQ ID NO: 13:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Ala Arg Ile Arg Ala Arg Gly Ser Ser Thr Val Asp Leu Gln Pro
1               5                  10                  15

Lys Leu Ile Ile Asp
                20
```